United States Patent [19]

Li

[11] Patent Number: 5,002,550

[45] Date of Patent: Mar. 26, 1991

[54] SUTURE ANCHOR INSTALLATION TOOL

[75] Inventor: Lehmann K. Li, Wellesley, Mass.

[73] Assignee: Mitek Surgical Products, Inc., Norwood, Mass.

[21] Appl. No.: 476,307

[22] Filed: Feb. 7, 1990

Related U.S. Application Data

[63] Continuation-in-part of Ser. No. 449,118, Dec. 8, 1989, Pat. No. 4,946,468, which is a continuation of Ser. No. 362,004, Jun. 6, 1989.

[51] Int. Cl.⁵ ............................................. A61B 17/00
[52] U.S. Cl. .................................. 606/139; 606/232; 606/144
[58] Field of Search ............... 606/139, 232, 72-78, 606/142, 144

[56] References Cited

U.S. PATENT DOCUMENTS

| | | | |
|---|---|---|---|
| 4,006,747 | 2/1977 | Kronenthal et al. | 606/144 |
| 4,235,238 | 11/1980 | Ogiu et al. | 606/145 |
| 4,586,502 | 5/1986 | Bedi et al. | 606/144 |
| 4,669,473 | 6/1987 | Richards et al. | 602/220 |

Primary Examiner—Randall L. Green
Assistant Examiner—Gary Jackson
Attorney, Agent, or Firm—Schiller, Pandiscio & Kusmer

[57] ABSTRACT

A new and improved suture anchor of the sort adapted to anchor an intermediate portion of a piece of conventional suture in bone, and a new and improved installation tool for deploying the same, said installation tool being adapted to releasably hold at least one curved needle which is attached to said piece of conventional suture.

21 Claims, 9 Drawing Sheets

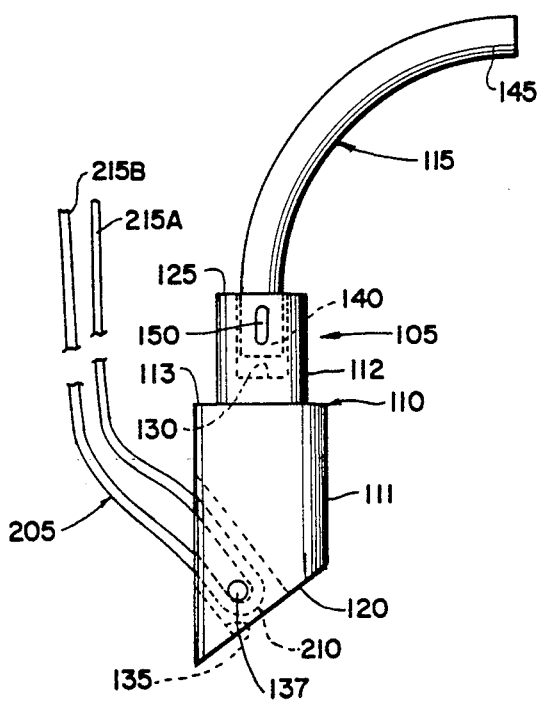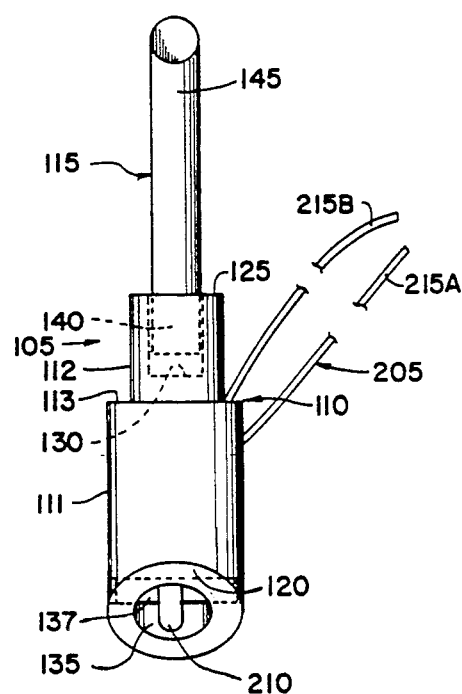

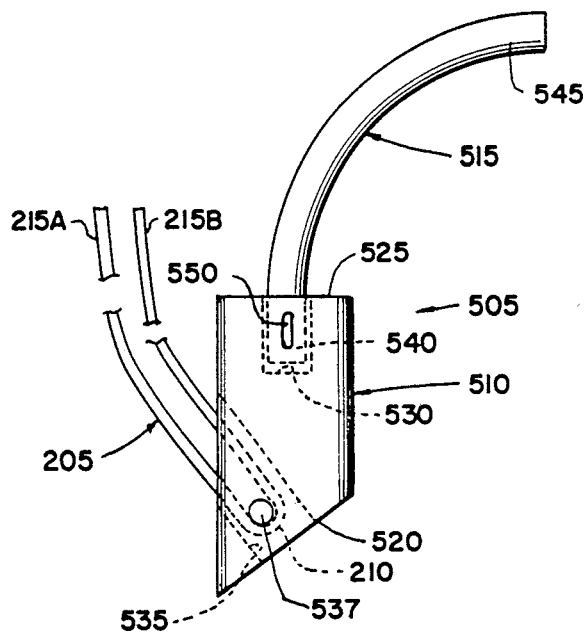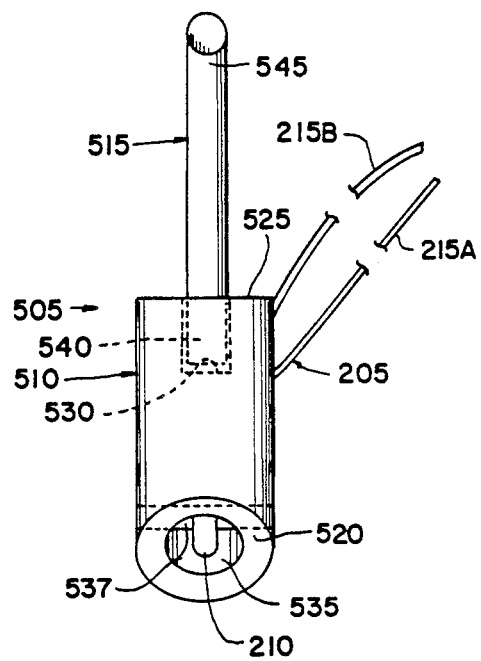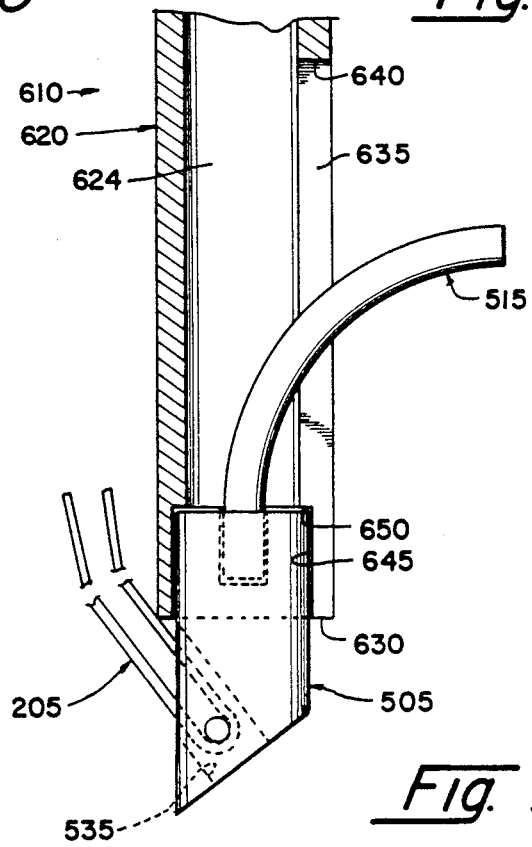

SUTURE ANCHOR INSTALLATION TOOL

REFERENCE TO PENDING PATENT APPLICATION

This application is a continuation-in-part of pending U.S. patent application Ser. No. 449,118, filed 12/8/89 by Lehmann K. Li, now U.S. Pat. No. 4,946,468, which is a continuation of U.S. patent application Ser. No. 362,004, filed 6/6/89 by Lehmann K. Li.

FIELD OF THE INVENTION

This invention relates to surgical devices in general, and more particularly to suture anchors of the sort adapted to anchor one portion of a piece of conventional suture in bone, and installation tools for deploying the same.

BACKGROUND OF THE INVENTION

Numerous devices are currently available to attach objects to bone. More specifically, screws, staples, cement and sutures have all been used to attach soft tissue (e.g. ligaments, tendons, muscles, etc.), bone and inanimate objects (e.g. prostheses) to bone.

In certain situations it is desirable to anchor one end of a piece of conventional suture in bone, leaving the other end of the piece of suture residing free outside the bone so that the free end of the suture can then be used to attach the desired object (e.g. a ligament or prosthesis) to the bone.

Suture anchors for anchoring one end of a piece of conventional suture in bone, and installation tools for deploying the same, are described and illustrated in pending U.S. Patent Application Ser. No. 051,367, filed 5/18/87 by Roland F. Gatturna et al. for "Suture Anchor", pending U.S. Patent Application Ser. No. 132,940, filed 12/15/87 by James E. Nicholson et al. for "Suture Anchor Installation Tool", and pending U.S. Patent Application Ser. No. 308,318, filed 2/8/89 by Roland F. Gatturna.

Still other suture anchors and suture anchor installation tools are described and illustrated in U.S. Pat. No. 4,632,100, issued 12/30/86 to Somers et al., U.S. Pat. No. 4,738,255, issued 4/19/88 to Goble et al., and U.S. Pat. No. 4,741,330, issued 5/3/88 to Hayhurst.

In certain circumstances it may be desirable to have more than one suture end residing free outside the bone for use in attaching the desired object or objects to the bone. In this situation, with the suture anchors of the above-identified pending U.S. Patent Applications Ser. Nos. 051,367 and 132,940, as well as with the suture anchors of the above-identified U.S. Pat. Nos. 4,632,100, 4,738,255 and 4,741,330, the only recourse is to implant more than one suture anchor to provide the desired more than one free suture ends. This technique can have obvious disadvantages.

The above-identified U.S. Patent Application Ser. No. 308,318 discloses a suture anchor wherein two separate sutures are attached to a single suture anchor, thereby yielding two free suture ends for each suture anchor deployed, but this arrangement requires that two separate sutures be threaded through the anchor's suture-receiving bore and thereafter tied to one another so as to affix the two separate sutures to the suture anchor. This threading and tying operation can be relatively time-consuming to achieve. In addition, this attachment technique creates the additional risk that the sutures can become separated from the suture anchor if the knot should fail.

Installation tools for deploying suture anchors of the sort described above are described and illustrated in U.S. Patent Applications Ser. Nos. 051,367, 132,940 and 308,318. Other installation tools for deploying suture anchors of the sort described above are described and illustrated in U.S. Patent Application Ser. No. 449,118, which is a continuation of U.S. Patent Application Ser. No. 362,004.

In the suture anchor installation tools described and illustrated in U.S. Patent Application Ser. No. 449,118, the installation tools are adapted to store an intermediate portion of suture in an interior chamber inside the installation tool until the suture anchor is deployed in bone, whereupon the intermediate portion of the suture may be pulled from its storage position within the installation tool. In addition, in the suture anchor installation tools described and illustrated in U.S. Patent Application Ser. No. 449,118, the installation tools are adapted to receive a pair of surgical needles (attached to the suture) in a pair of grooves formed in the outer surface of the installation tool until the suture anchor is deployed in bone, whereupon the surgical needles may be pulled from their storage positions in the grooves and used to attach tissue or other objects to the bone holding the suture anchor.

OBJECTS OF THE INVENTION

The principal object of the present invention is to provide a new and improved suture anchor installation tool for deploying suture anchors of the sort described and illustrated in U.S. Patent Applications Ser. Nos. 051,367, 132,940, 308,318 and 449,118.

Still another object is to provide a suture anchor installation tool which is an improvement over the suture anchor installation tools described and illustrated in U.S. Patent Application Ser. No. 449,118.

Yet another object is to provide a suture anchor installation tool which is adapted to receive a pair of surgical needles in a pair of grooves formed in the outer surface of the installation tool, and which provides means for selectively covering and uncovering the pair of surgical needles received in the pair of grooves.

Still another object is to provide a suture anchor installation tool which includes improved means for releasably holding a pair of surgical needles in a pair of grooves formed in the outer surface of the installation tool.

Yet another object is to provide a new and improved suture anchor system for anchoring a piece of conventional suture in bone.

And another object is to provide a new and improved method for anchoring a piece of conventional suture in bone.

SUMMARY OF THE INVENTION

These and other objects of the invention are achieved through the use of a novel suture anchor installation tool of the sort adapted to deploy a suture anchor of the sort comprising (a) a coupling member, (b) at least one barb, the barb having a first end and a second end and being curved in its normal unstressed state and being capable of being elastically deformed to a substantially straight configuration, the barb being attached to the coupling member so that the second end of the barb is substantially displaced from the coupling member when the barb is in its normal unstressed state but is capable of being aligned with the coupling member when the barb is deformed to a substantially straight length, and (c) attachment means for attaching a portion of a piece of conventional suture to the suture anchor, wherein the suture anchor installation tool comprises a first body portion and a second body portion, the first body portion having a first end and a second end, the first end of the first body portion being hollow and having a slot extending from the first end of the first body portion towards the second end of the first body portion, with the first end of the first body portion being sized to accommodate a portion of the coupling member, and the slot being sized to accommodate the barb of the suture anchor, and the second body portion having a first end and a second end, the second body portion having a hollow interior and an opening leading to the hollow interior, the hollow interior being sized to accommodate an intermediate portion of a suture attached to the suture anchor, and the opening being sized to accommodate at least one cross-section of the suture, with the second end of the first body portion being joined to the first end of the second body portion, the second body portion further including needle receiving means for receiving at least one surgical needle attached to the suture in an outer surface of the second body portion, and the second body portion further including needle covering means for selectively covering and uncovering the needle receiving means.

BRIEF DESCRIPTION OF THE DRAWINGS

Still other objects and features of the present invention will be more fully described or rendered obvious in the following detailed description of the invention, which is to be considered together with the accompanying drawings wherein like numbers refer to like parts and further wherein:

FIG. 1 is a side view in elevation showing one side of a suture anchor formed in accordance with the present invention;

FIG. 2 is a side view in elevation showing another side of the suture anchor shown in FIG. 1, the suture anchor shown in FIG. 2 having been rotated 90 degrees from the position shown in FIG. 1;

FIG. 13 is a side view in elevation showing one side of an alternative form of suture anchor formed in accordance with the present invention;

FIG. 14 is a side view in elevation showing another side of the suture anchor shown in FIG. 13, the suture anchor shown in FIG. 14 having been rotated 90 degrees from the position shown in FIG. 13;

FIG. 15 is a partial side view in elevation showing the suture anchor of FIGS. 13 and 14, with a suture attached, loaded into a modified form of the suture anchor installation tool;

DETAILED DESCRIPTION OF THE INVENTION

Figure 3:
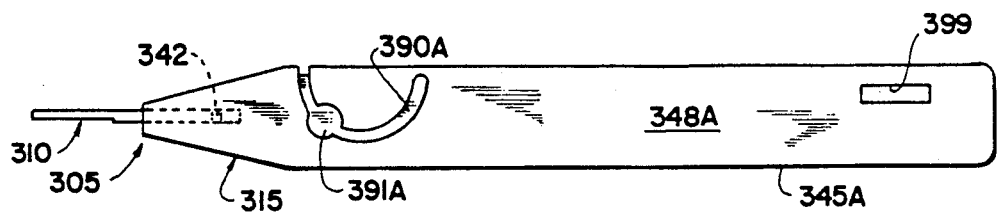
FIG. 3 is a side view in elevation showing the left side of a suture anchor installation tool formed in accordance with the present invention.

Looking first at FIGS. 1 and 2, there is shown a suture anchor 105 formed in accordance with the present invention. Suture anchor 105 generally comprises a coupling member 110 and a barb 115.

Coupling member 110 comprises a piece of 6AL4V titanium alloy having a cylindrical lower portion 111 and a cylindrical upper portion 112. Cylindrical lower portion 111 has a diameter which is greater than the diameter of cylindrical upper portion 112, whereby a shoulder 113 is formed at the junction of the coupling member's lower portion 111 and its upper portion 112. Coupling member 110 has a first end surface 120 disposed at one end of lower portion 111 and a second end surface 125 disposed at the opposite end of upper portion 112. First end surface 120 is disposed at an angle of approximately 30 degrees to the coupling member's longitudinal axis, and second end surface 125 is disposed at a right angle to the coupling member's longitudinal axis, as shown. The coupling member's upper portion 112 has a blind hole 130 opening on second end surface 125, and the coupling member's lower portion 111 has a bore 135 extending at an angle between the coupling member's side wall and its bottom end surface 120, as shown. Bore 135 extends at a right angle to the coupling member's bottom end surface 120. A pin 137 is mounted to opposing side walls of the coupling member near bottom end surface 120 so that the pin extends across the middle of bore 135, as shown.

Barb 115 comprises a curved length of nickel titanium alloy having a first end 140 and a second end 145. Barb 115 comprises an arc of approximately 120 degrees. Barb 115 is attached to the coupling member by fitting the barb's first end 140 in the coupling member's blind hole 130, whereby the barb's second end 145 extends upward and outward from the coupling member. The coupling member's upper portion 112 is then crimped inward at one or more points as shown at 150 (FIG. 1) to lock barb 115 to the coupling member. Barb 115 is made of such a nickel titanium alloy that it is capable of being elastically deformed to a substantially straight length when desired (i.e., so that the barb's second end 145 is aligned with its first end 140, as well as with the opposite end surfaces 120 and 125 of the coupling member). By way of example, barb 115 may be made out of binary nitinol such as that sold by Raychem Corporation of Menlo Park, California and Furukawa of Japan, or it might be made out of ternary nitinol such as that sold by Raychem Corporation and described in U.S. Pat. No. 4,505,767, issued 3/19/85 to Quinn. It is noted that the transition temperature of the nitinol must be below normal body temperature, such that the arc is substantially transitioned into the martensite state and exhibits elastic behavior on insertion into bone.

Still looking at FIGS. 1 and 2, a suture 205 having an intermediate portion 210 and opposite ends 215A, 215B is attached to suture anchor 105 by threading the suture around anchor pin 137 so that the intermediate portion 210 of the suture is supported by anchor pin 137 while the two ends 215A, 215B of the suture are left free of the suture anchor so that they may be used to attach the desired object or objects to bone when the suture anchor is deployed in the bone. Preferably the dimensions of the suture anchor's bore 135 and pin 137 are coordinated with the dimensions of suture 205 so that the suture may be easily threaded around pin 137 and yet will be snugly received in the suture anchor when it is threaded around anchor pin 137, so that the suture will remain in place relative to the suture anchor.

Looking next at FIGS. 3-8, there is shown a suture anchor installation tool 305 formed in accordance with the present invention. Suture anchor installation tool 305 generally comprises a cannula 310 and a handle 315.

Figure 6:
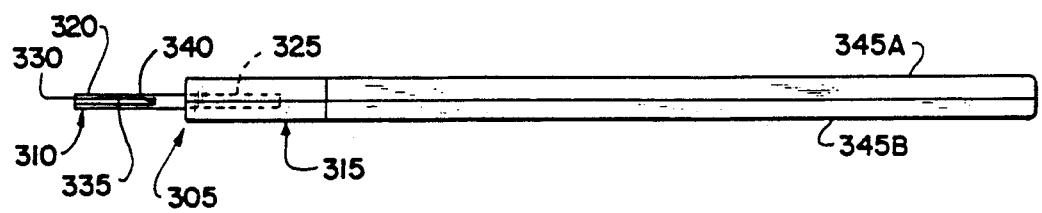
FIG. 6 is a bottom view showing the bottom side of the suture anchor installation tool shown in FIG. 3.
Figure 7:
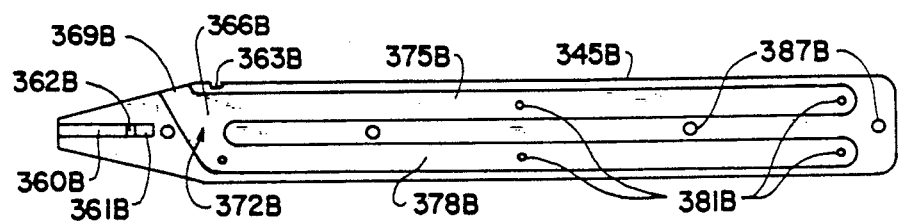
FIG. 7 is a side view in elevation showing the interior configuration of the right half of the suture anchor installation tool shown in FIG. 3.
Figure 8:
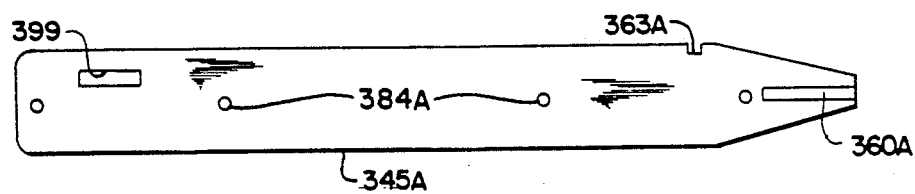
FIG. 8 is a side view in elevation showing the interior configuration of the left half of the suture anchor installation tool shown in FIG. 3.

As best seen in FIGS. 3 and 6, cannula 310 comprises a first end 320 and a second end 325. First end 320 terminates in a front end surface 330. Cannula 310 is hollow and has a longitudinally-extending front slot 335 (FIG. 6) formed in its side wall. Front slot 335 begins at front end surface 330 and terminates in a rear end surface 340. Cannula 310 also has a smaller opening 342 (FIG. 3) formed in its side wall at its rear end 325. Opening 342 is disposed 90 degrees from front slot 335, for reasons which will hereinafter be made clear.

Suture anchor installation tool 305 is intended to be used to install the suture anchor 105 previously described, and to this end the dimensions of cannula 310 are coordinated with the dimensions of suture anchor 105. More specifically, cannula 310 is sized relative to suture anchor 105 so that (a) the first end 320 of cannula 310 has an outer diameter which is smaller than, equal to or just slightly larger than the outer diameter of the suture anchor's lower portion 111, so that the smallest possible hole may be formed in the bone which is to receive the bone anchor, (b) the first end 320 of cannula 310 has an internal diameter which is slightly larger than the outer diameter of the suture anchor's upper portion 112, but slightly smaller than the outer diameter of the suture anchor's lower portion 111, whereby the suture anchor's upper portion 112 may be snugly received in the interior of cannula 310 but the suture anchor's lower portion 111 may not, with the cannula's front end surface 330 engaging the suture anchor's shoulder 113, as will hereinafter be described in further detail, (c) the cannula's slot 335 has a width slightly larger than the diameter of the suture anchor's barb 115, so that the barb will fit between the walls of first end 320 which define slot 335, as will hereinafter be described in further detail, and (d) slot 335 has a length sufficient to accommodate the suture anchor's barb 115 when the barb is bent backwards into the cannula during deployment of the suture anchor, as will hereinafter be described in further detail.

Figure 4:
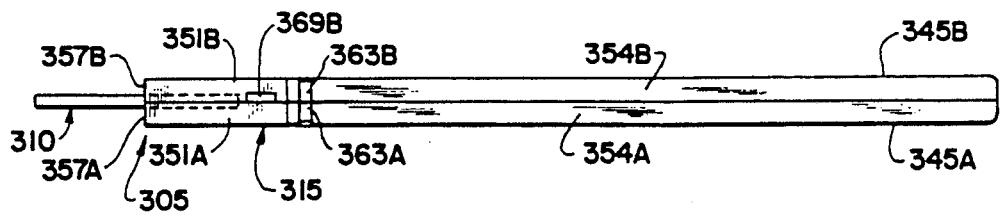
FIG. 4 is a top view showing the top side of the suture anchor installation tool shown in FIG. 3.
Figure 5:
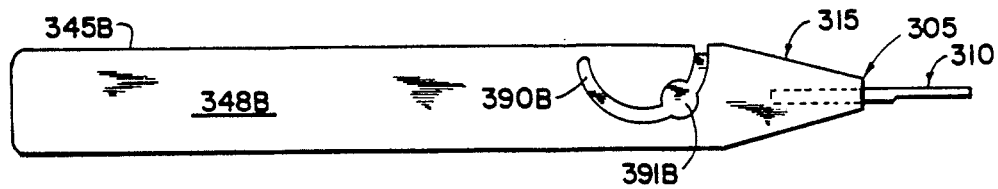
FIG. 5 is a side view in elevation showing the right side of the suture anchor installation tool shown in FIG. 3.

Still looking now at FIGS. 3-8, handle 315 comprises two members 345A, 345B which snap together in the manner shown to form a single handle unit having a left side surface 348A (FIG. 3), a right side surface 348B (FIG. 5), a pair of coplanar adjacent sloped surfaces 351A, 351B (FIG. 4), a pair of coplanar, adjacent top surfaces 354A, 354B (FIG. 4), and a pair of coplanar, adjacent front surfaces 357A, 357B (FIG. 4).

Member 345A is relieved at 360A (FIG. 8), and member 345B is relieved at 360B and at 361B so as to form a land 362B (FIG. 7), so that when the two members are joined together as will hereinafter be described in further detail, a blind hole type of interior chamber (hereinafter referred to as chamber 360A/360B) will be defined in the handle which opens on the two front surfaces 357A, 357B. Chamber 360A/360B is sized so as to receive the second end 325 of cannula 310, with the cannula's opening 342 receiving the land 362B, whereby cannula 310 and handle 315 can be attached to one another to function as a single unit, as will hereinafter be described in further detail.

Member 345A is also relieved at 363A (FIG. 8), and member 345B is relieved at 363B (FIG. 7), so that when the two members are joined together as will hereinafter be described in further detail, a surface groove (hereinafter referred to as groove 363A/363B) will be defined in the handle in top surfaces 354A, 354B (FIG. 4). Surface groove 363A/363B is formed so as to have a diameter somewhat larger than the diameter of a suture used with the installation tool, as will hereinafter be described in further detail.

Member 345B is also relieved at 366B (FIG. 7) so that when the two members are joined together as will hereinafter be described in further detail, an opening 369B (FIGS. 4 and 7) communicating with an interior chamber 372B (FIG. 7) will be formed, wherein opening 369B opens on sloped surface 351B (FIG. 4). More specifically, member 345B is relieved at 366B so that opening 369B is somewhat larger than four diameters of a suture being used with the tool, and so that a pair of parallel, elongated subchambers 375B, 378B are formed in the handle, with a plurality of dimples 381B rising slightly from the floor of each of the subchambers 375B, 378B. Inasmuch as chamber 372B serves to store an intermediate length of suture when a suture anchor is attached to the suture anchor installation tool, and inasmuch as dimples 381B serve to releasably hold the stored suture in place within the handle chamber, dimples 381B are sized so that at least two widths of suture can pass between each of the dimples and the surrounding wall of the subchambers, and dimples 381B are sized so that they rise only slightly above the floor of the subchambers so that the suture can slip over the top of the dimples during deployment, as will hereinafter be described in further detail.

Member 345A is also formed with a plurality of holes 384A (FIG. 8), and member 345B is also formed with a plurality of posts 387B (FIG. 7), whereby when it is desired to join handle member 345A to handle member 345B, the two members may be press fit together in the manner shown, with posts 387B seating in holes 384A, as will hereinafter be described in further detail.

Members 345A, 345B are also formed with curved surface grooves 390A, 390B in their side surfaces 348A, 348B (FIGS. 3 and 5), to receive and securely hold a pair of curved surgical needles therein, as will hereinafter be described in further detail. To this end, it will be appreciated that by forming surface grooves 390A, 390B with slightly smaller radii of curvature than the surgical needles which are to be held, and by squeezing the surgical needles slightly during insertion so as to reduce their radii of curvature, the surgical needles can be "spring loaded" into the grooves 390A, 390B so as to assure that the needles will be securely seated in the grooves. Surface grooves 390A, 390B include expanded portions 391A, 391B, as shown.

Member 345A also includes a horizontally elongated slot 399. Slot 399 is positioned to coincide with elongated subchamber 375B of member 345B, whereby access can be gained to the subchamber via slot 399, as will hereinafter be described in further detail.

Figure 9:
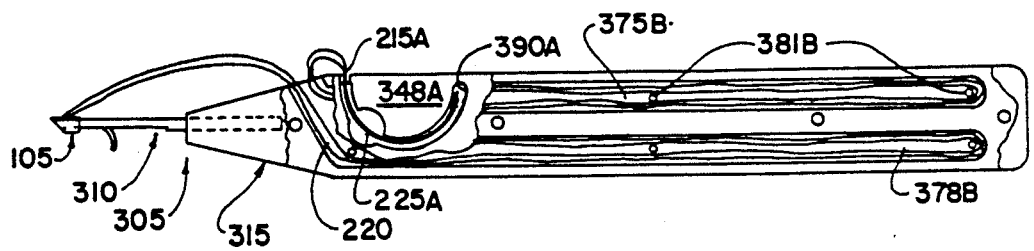
FIG. 9 is a side view in elevation, partially broken away, showing the suture anchor of FIGS. 1 and 2, with a suture attached, loaded into the suture anchor installation tool of FIGS. 3-8, the view being taken from the left side of the suture anchor installation tool.

Prior to using the foregoing apparatus in a surgical procedure, the apparatus is assembled as follows. First, a suture anchor 105, a suture 205, a cannula 310 and handle members 345A, 345B are assembled. Then the suture 205 having free ends 215A, 215B is attached to the suture anchor 105 by threading the suture around anchor pin 137 so that the intermediate portion 210 of the suture is supported by anchor pin 137 while the two ends 215A, 215B of the suture are left free of the suture anchor. Then suture anchor 105 is attached to the installation tool's cannula 310 by fitting the suture anchor's upper portion 112 into the front end of the cannula, with the cannula's front end surface 330 engaging the suture anchor's shoulder 113 and the suture anchor's barb 115 being accommodated in the cannula's slot 335. Next the rear end 325 of cannula 310 is positioned into the appropriate relieved portions of member 345B (i.e., the rear end 325 of the cannula is fit into housing chamber 360A/360B, with the cannula's rear opening 342 receiving handle land 362B, whereby the cannula's slot 335 will be oriented downward, 180 degrees away from the handle's top surfaces 354A, 354B). Next, an intermediate portion 220 of the suture is coiled into subchambers 375B, 378B around dimples 381B, with the suture doubling back on itself through opening 369B so as to leave the suture ends 215A, and 215B free outside handle 315, as shown in FIG. 9. Then members 345A and 345B are snapped together, so that suture anchor 105, cannula 310 and handle 315 will be united together as a single unit. Next surgical needles 225A, 225B (only one of which, 225A, is shown, in FIG. 9) are attached to the free ends 215A, 215B of the suture, and these needles are placed in the handle's surface slots 390A, 390B for storage therein until required. Then a crochet needle type of tool is inserted into slot 399 and manipulated so as to pull any excess outside suture back into the handle, and also so as to pull the suture taut within the handle.

Preferably, handle member 345A is formed out of a transparent plastic so that the suture contained inside the housing can be clearly observed during assembly and subsequent use.

The foregoing components may then be packaged, sterilized and stored until required during surgery.

Figure 10:
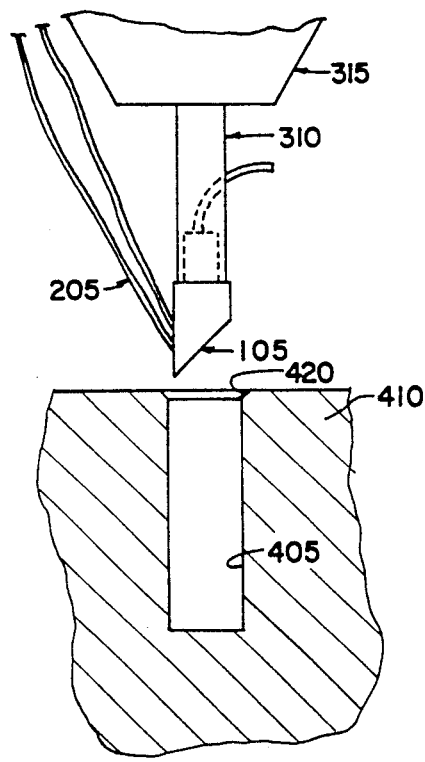
FIGS. 10-12 are a series of schematic views showing the suture anchor of FIGS. 1 and 2 being deployed into a bone hole using the suture anchor installation tool of FIGS. 3-8.
Figure 11:
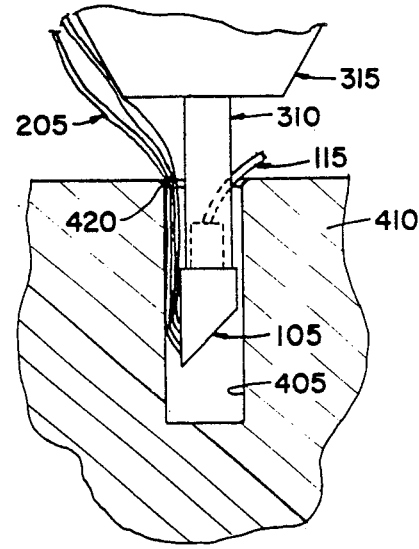
Figure 12:
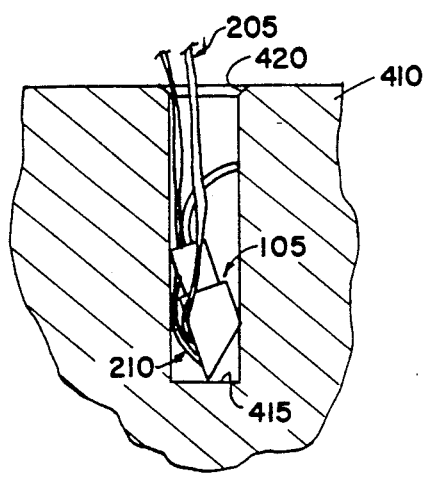

During surgery, the apparatus is used as follows. A hole 405 (FIG. 10) is first formed in a bone 410 which is to receive the suture anchor 115. As seen in FIGS. 10-12, bone 410 is preferably chamfered about the top end of hole 405 at 420 so as to eliminate any sharp surface which might cut the suture. Then the distal end of the suture anchor installation tool is pressed down into the predrilled hole 405 in bone 410 (FIGS. 10 and 11) until the leading tip of the suture anchor bottoms out on bone surface 415 (FIG. 12). As the distal end of the suture anchor installation tool forces the suture anchor down into the bone, the suture anchor's barb 115 engages the side wall of the bone, forcing the barb to retract inwards, into the cannula slot 335, so that the suture anchor and the cannula portion of the suture anchor installation tool can enter bone hole 405. As the suture anchor passes by the hard cortical outer portion of the bone and enters the softer cancellous interior region of the bone, the barb's resilient nature will cause it to bend itself back into a curved length, with the barb acting as a resilient hook to engage adjacent bone matter. When the suture anchor reaches the bone surface 415, the installation tool is withdrawn upward, whereupon engagement of the suture anchor's barb 115 with the surrounding bone causes the suture anchor to separate from the departing installation tool, so that the suture anchor remains securely anchored in position within the bone, keeping the intermediate portion 210 of suture 205 captured in place inside the bone. It is to be appreciated that as the retreating installation tool withdraws from the emplaced suture anchor, the superior mechanical strength and elasticity of barb 115 will cause the barb to attempt to return to its unstressed, curved state, and this action will kick the suture anchor sideways somewhat, as shown in FIG. 12, causing a multipoint engagement of the suture anchor with the surrounding walls of bone 410. This has the effect of consistently and reliably further securely anchoring the suture anchor in the bone.

It is also to be appreciated that as the retreating installation tool withdraws from bone hole 405 and thereby separates from the emplaced suture anchor, the intermediate portion 220 of the suture (previously stored within the interior of handle 315, as described above) will play out from the installation tool's cavity 372B via opening 369B. Thereafter the needles 225A, 225B (attached to the free ends 215A, 215B of the suture and securely mounted in handle slots 390A, 390B as noted above) are freed from the handle and used, in conjunction with the associated suture, to fasten the desired object or objects to the bone. It is to be appreciated that the expanded portions 391A, 391B of surface grooves 390A, 390B facilitate removal of the needles from the slots, by permitting forceps or another tool to grasp the needles and separate them from handle 315.

(It is, of course, to be noted that the device could be provided without needles being attached to the suture until the suture anchor and suture anchor installation tool are unpackaged in the operating room; if this is the case, the surgeon simply attaches the needles to the suture upon unpackaging.)

Preferably the installation tool's cannula 310 and handle 315 are sized and assembled so that the installation tool's front surfaces 357A, 357B will act as natural stop members to inhibit further penetration of the tool into bone 410, in the event that hole 405 is formed too deep in the bone.

Figure 12A:
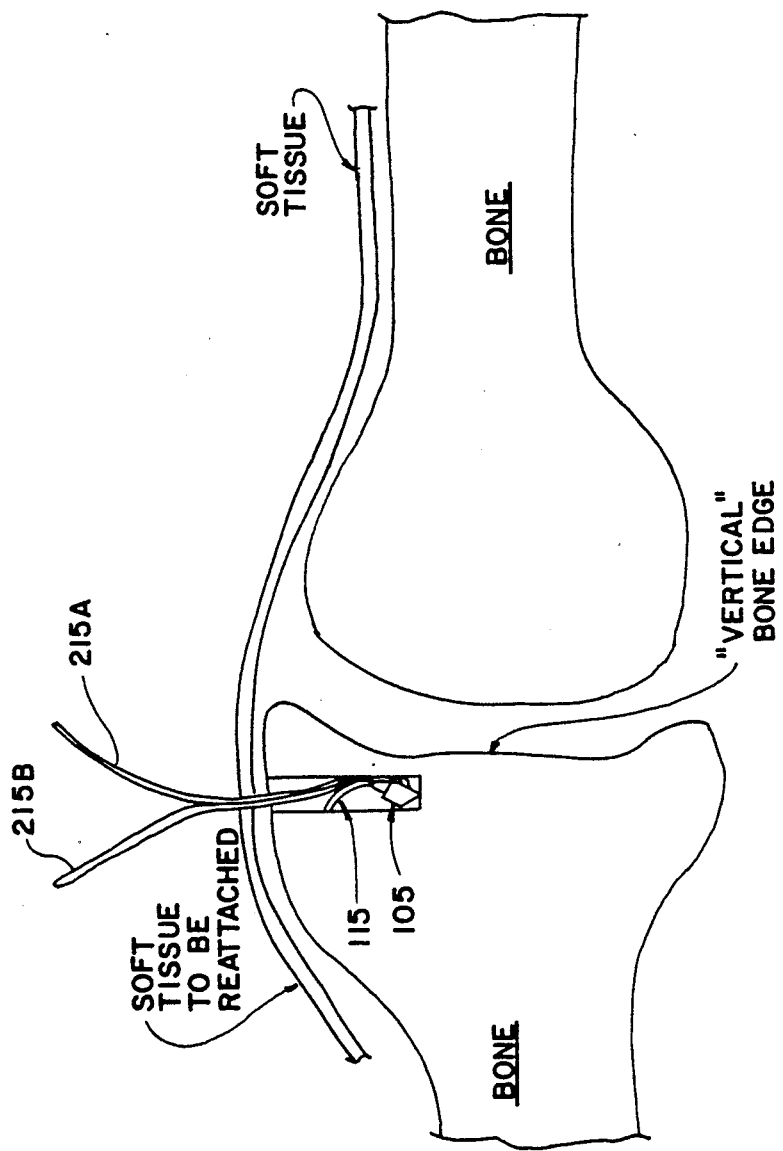
FIG. 12A shows a typical situation in which a suture anchor is used to reattach soft tissue to bone.

It should also be appreciated that the construction of the present suture anchor installation tool provides the additional feature of the user always knowing the direction the barb extends in during deployment. More specifically, it will be appreciated that by virtue of the fact that the cannula's slot 335 always faces directly downward (i.e., directly away from the handle's top surfaces 354A, 354B), the user holding handle 315 will always know the orientation of the suture anchor's barb 115 relative to the suture anchor installation tool. Such a feature can be very important in situations where the suture anchor installation tool must set the suture anchor very close to a "vertical" bone edge, since in such situations the suture anchor should be deployed with its barb oriented directly away from the vertical bone edge so as to minimize any possibility the barb could project through the vertical bone edge (and hence extend out of the bone) during deployment. By way of illustration, FIG. 12A shows a typical situation in which soft tissue is being reattached to a bone with a suture anchor. In this situation it is desirable to place the suture anchor as close to the vertical bone edge as possible, so that the soft tissue being reattached can be reattached to the bone fairly close to the end of the bone. This necessitates placing the anchor-receiving bone hole fairly close to the vertical bone edge, so that the barb should be deployed so that it will spring away from the vertical bone edge during deployment and thereby avoid the possibility that the barb could poke through the vertical bone edge and into the joint as the barb returns to its curved orientation.

It should, of course, be appreciated that one or both of the suture anchor 105 and suture anchor installation tool 305 described above could be modified somewhat without departing from the scope of the present invention.

Thus, for example, suture anchor 105 could have its coupling member 110 formed out of a material other than 6AL4V titanium alloy, and its barb 115 formed out of a material other than nickel titanium alloy. By way of example, coupling member 110 could be formed out of titanium and its alloys, ceramics, plastics, stainless steel and other suitable bio-compatible materials. By way of further example, barb 115 could be formed out of titanium and its alloys, and stainless steel. Nitinol is currently the preferred material due to its superior elastic properties.

It is also anticipated that the installation tool's cannula 310 might be formed out of a cylindrical member which is hollow on its leading tip only, and which is solid on its trailing end. Of course, if this is the case, a different method for attaching the rear end 325 of cannula 310 to housing 315 must be used, since cannula opening 342 will no longer be available to mate with handle land 362B, as previously described. In this case cannula 310 might simply be glued to handle 315.

It is also anticipated that the suture anchor might be modified somewhat from the design shown in FIGS. 1 and 2 so that the suture anchor's coupling member comprises a body of singular diameter.

More specifically, and looking now at FIGS. 13 and 14, there is shown a suture anchor 505 which generally comprises a coupling member 510 and a barb 515.

Coupling member 510 comprises a piece of 6AL4V titanium alloy having a cylindrical body characterized by a first end surface 520 and a second end surface 525 disposed at the opposite end of the coupling member. First end surface 120 is disposed at an angle of approximately 30 degrees to the coupling member's longitudinal axis, and second end surface 125 is disposed at a right angle to the coupling member's longitudinal axis, as shown. The coupling member has a blind hole 530 opening on second end surface 525, and the coupling member has a bore 535 extending at an angle between the coupling member's side wall and its bottom end surface 520, as shown. Bore 535 extends at a right angle to the coupling member's bottom end surface 520. A pin 537 is mounted to opposing side walls of the coupling member near bottom end surface 520 so that the pin extends across the middle of bore 535, as shown.

Barb 515 comprises a curved length of nickel titanium alloy having a first end 540 and a second end 545. Barb 515 comprises an arc of approximately 120 degrees. Barb 515 is attached to the coupling member by fitting the barb's first end 540 in the coupling member's blind hole 530, whereby the barb's second end 545 extends upward and outward from the coupling member. The coupling member's body is then crimped inward at one or more points as shown at 550 (FIG. 13) to lock barb 515 to the coupling member. Barb 515 is made of such a nickel titanium alloy that it is capable of being elastically deformed to a substantially straight length when desired (i.e., so that the barb's second end 545 is aligned with its first end 540, as well as with the opposite end surfaces 520 and 525 of the coupling member). By way of example, barb 515 may be made out of binary nitinol such as that sold by Raychem Corporation of Menlo Park, California and Furukawa of Japan, or it might be made out of ternary nitinol such as that sold by Raychem Corporation and described in U.S. Pat. No. 4,505,767, issued 3/19/85 to Quinn.

Still looking at FIGS. 13 and 14, a suture 205 having an intermediate portion 210 and opposite ends 215A, 215B is attached to suture anchor 505 by threading the suture around anchor pin 537 so that the intermediate portion 210 of the suture is supported by anchor pin 537 while the two ends 215A, 215B of the suture are left free of the suture anchor so that they may be used to attach the desired object or objects to bone when the suture anchor is deployed in the bone. Preferably the dimensions of the suture anchor's bore 535 and pin 537 are coordinated with the dimensions of suture 205 so that the suture may be easily threaded around pin 537 and yet will be snugly received in the suture anchor when it is threaded around anchor pin 537, so that the suture will remain in place relative to the suture anchor.

It will be appreciated that suture anchor installation tool 305 must be modified slightly to work in conjunction with the suture anchor 505 shown in FIGS. 13 and 14. More specifically, the design of the front end 320 of the installation tool's cannula 310 must be modified slightly from that shown in FIGS. 3-12 so that the cannula can mate with and properly support the modified form of suture anchor 505 shown in FIGS. 13 and 14 during deployment of the suture anchor.

Looking next at FIG. 15, suture anchor 505 is shown in engagement with the front end 620 of a cannula 610 of an installation tool; only the front end 620 of the cannula is shown, inasmuch as the remainder of the cannula is identical to the rear end of the cannula 310 already described and illustrated. It will be appreciated that the unshown portion of cannula 610 mates with an installation tool handle 305 such as that already described and illustrated, in the manner already described and illustrated.

The front end 620 of cannula 610 is characterized by an internal bore 624 which has a diameter less than the diameter of the suture anchor's coupling member 510, and a counterbore 645 which opens on the cannula's distal end 630 and terminates in an internal shoulder 650. Counterbore 645 is sized to have a diameter slightly greater than the diameter of the suture anchor's coupling member 510, and shoulder 650 is positioned a sufficient distance from distal end 620 to allow a portion of the suture anchor's coupling member to be received within the cannula's counterbore 645, with the suture anchor's bore 535 still being completely exposed, as shown. A slot 635 terminating in a rear surface 640 is provided to accommodate the suture anchor's barb 515.

Except for the foregoing differences in construction, and except for the foregoing differences in the way coupling member 515 mates with cannula 610, it will be appreciated that suture anchor 505 and cannula 610 operate in substantially the same manner as suture anchor 105 and cannula 310 previously described.

Figure 16:
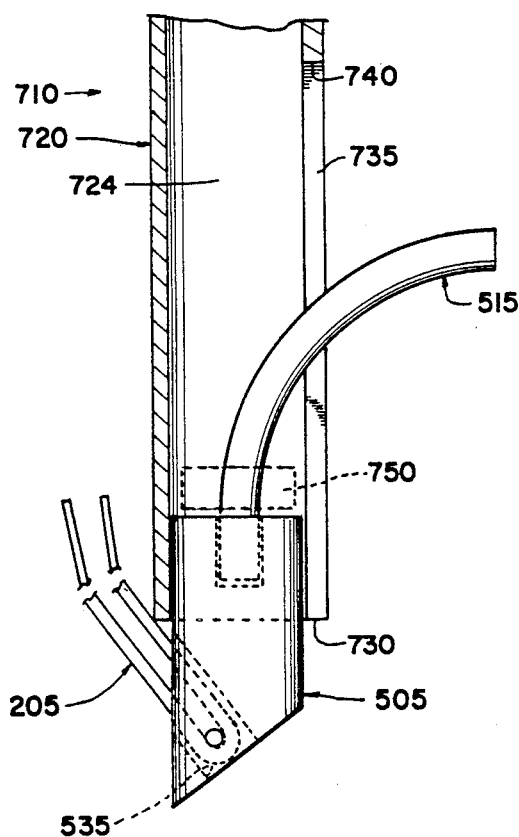
FIG. 16 is a partial side view in elevation showing the suture anchor of FIGS. 13 and 14, with a suture attached, loaded into another modified form of the suture anchor installation tool.

Still another possible modification of the installation tool's front end 320 is shown in FIG. 16. As seen in FIG. 16, suture anchor 505 is shown in engagement with the front end 720 of a cannula 710 of an installation tool; only the front end 720 of the cannula is shown, inasmuch as the remainder of the cannula is identical to the rear end of cannula 310 already described and illustrated. It will be appreciated that the unshown portion of cannula 710 mates with an installation tool handle 305 such as that already described and illustrated, in the manner already described and illustrated.

The front end 720 of cannula 710 is characterized by an internal bore 724 which has a diameter slightly greater than the suture anchor's coupling member 510. Cannula 710 terminates in a front end surface 730, and has one or more radially intruding crimps 750 which serve as a stop for engaging the upper surface of the cannula and preventing it from riding up into the interior of the cannula. Crimps 750 are positioned so that a portion of the suture anchor's coupling member can be received within the cannula's bore 724, with the suture anchor's bore 535 still being completely exposed, as shown. A slot 735 terminating in a rear surface 740 is provided to accommodate the suture anchor's barb 515.

Except for the foregoing differences in construction, and except for the foregoing differences in the way coupling member 515 mates with cannula 710, it will be appreciated that suture anchor 505 and cannula 710 operate in substantially the same manner as suture anchor 105 and cannula 310 previously described.

Figure 17:
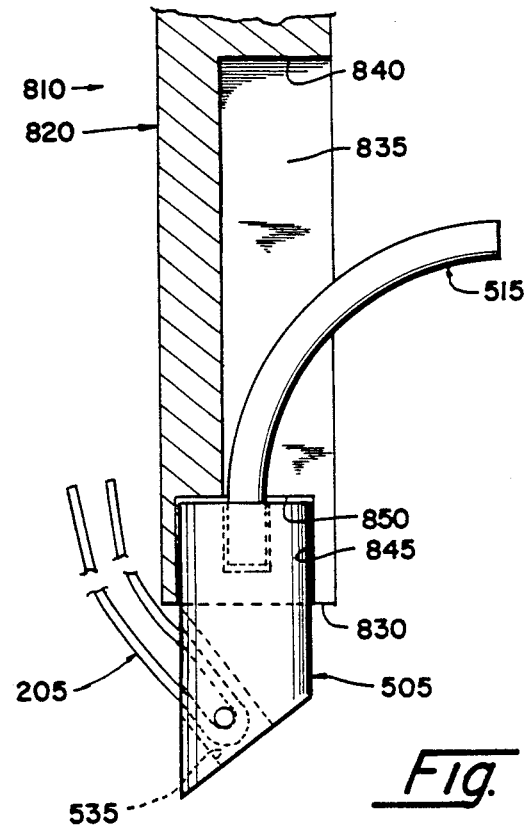
FIG. 17 is a partial side view in elevation showing the suture anchor of FIGS. 13 and 14, with a suture attached, loaded into still another modified form of the suture anchor installation tool.

Still another possible modification of the installation tool's front end 320 is shown in FIG. 17. As seen in FIG. 17, suture anchor 505 is shown in engagement with the front end 820 of a rod 810 of an installation tool; only the front end 820 of rod 810 is shown, inasmuch as the remainder of the rod is substantially identical to the rear end of cannula 310 already described and illustrated. It will be appreciated that the unshown portion of rod 810 mates with an installation tool handle 305 such as that already described and illustrated, in the manner already described and illustrated.

The front end 820 of rod 810 is characterized by a solid body having a front end surface 830. A blind hole 845 opens on front end surface 830 and terminates in a flat surface 850. Blind hole 845 has a diameter slightly greater than the suture anchor's coupling member 510, whereby a portion of the suture anchor's coupling member can be received within the rod's blind hole 845, with the suture anchor's bore 835 still being completely exposed, as shown. A slot 835, communicating with blind hole 845 and terminating in a rear surface 840, is provided to accommodate the suture anchor's barb 515.

Except for the foregoing differences in construction, and except for the foregoing differences in the way coupling member 515 mates with rod 810, it will be appreciated that suture anchor 505 and rod 810 operate in substantially the same manner as the suture anchor 105 and cannula 310 previously described.

It is also anticipated that one might increase the height of dimples 381B and make them out of a flexible material, whereby the suture will push over and then slip past the deflected dimples as it plays out of the interior of handle members 345A, 345B, rather than just slipping over the top of relatively low, rigid dimples. It is believed that such a construction might enhance holding the suture in place within the handle prior to deployment, and also provide increased tactile feedback as the suture plays out of the interior of the handle.

Looking next at FIGS. 18-25, there is shown an alternative form of suture anchor installation tool 902 formed in accordance with the present invention.

Suture anchor installation tool 902 generally comprises a cannula 904 and a handle 906.

Figure 18:
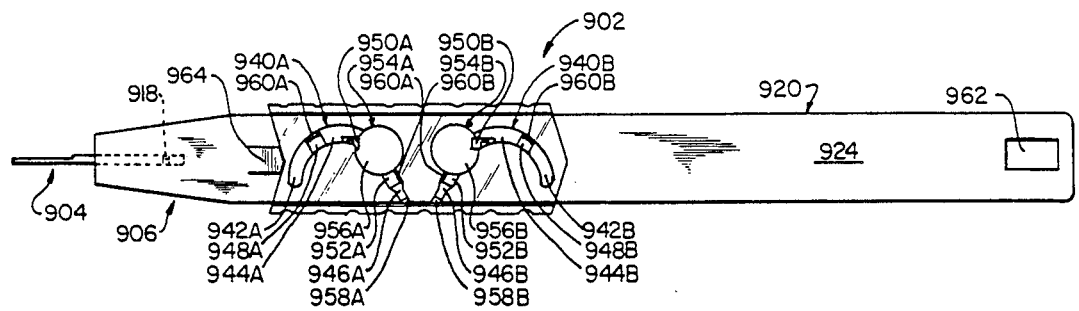
FIG. 18 is a side view in elevation showing the left side of an alternative form of suture anchor installation tool formed in accordance with the present invention.
Figure 21:
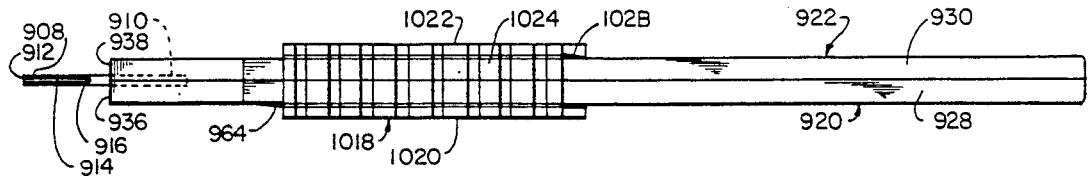
FIG. 21 is a top view showing the top side of the suture anchor installation tool shown in FIG. 18.

As best seen in FIGS. 18 and 21, cannula 904 is substantially identical to the cannula 310 previously described, i.e., it comprises a first end 908 and a second end 910, with first end 908 terminating in a front end surface 912. Cannula 904 is hollow and has a longitudinally-extending front slot 914 formed in its side wall. Front slot 914 begins at the cannula's front surface 912 and terminates in a rear end surface 916. Cannula 904 also has a smaller opening 918 formed in its side wall at its rear end 910. Opening 918 is disposed 90 degrees from front slot 914, for reasons which will hereinafter be made clear.

As with installation tool 305 previously described, installation tool 902 is intended to be used to install the suture anchor 105 previously described, and to this end the dimensions of cannula 904 are coordinated with the dimensions of suture anchor 105 in precisely the same manner that the dimensions of cannula 310 are coordinated with the dimensions of suture anchor 105. More specifically, cannula 904 is sized relative to suture anchor 105 so that:

(a) the first end 908 of cannula 904 has an outer diameter which is smaller than, equal to or just slightly larger than the outer diameter of the suture anchor's lower portion 111, so that the smallest possible hole may be formed in the bone which is to receive the bone anchor;

(b) the first end 908 of cannula 904 has an internal diameter which is slightly larger than the outer diameter of the suture anchor's upper portion 112, but slightly smaller than the outer diameter of the suture anchor's lower portion 111, whereby the suture anchor's upper portion 112 may be received in the interior of cannula 904 but the suture anchor's lower portion 111 may not;

(c) the cannula's slot 914 has a width slightly larger than the diameter of the suture anchor's barb 115, so that the barb can be received between the walls of first end 908 which define slot 914; and (d) slot 914 has a length sufficient to accommodate the suture anchor's barb 115 when the barb is bent backwards into the cannula during deployment of the suture anchor.

Looking next at FIGS. 18-25, handle 906 comprises left and right members 920 and 922, respectively, which mechanically snap together (or are glued or welded together) to form a single handle unit having a left side surface 924 (FIG. 18), a right side surface 926 (FIG. 20), a pair of coplanar adjacent top surfaces 928, 930 (FIG. 21), a pair of coplanar adjacent bottom surfaces 932, 934 (FIG. 19), and a pair of coplanar adjacent front surfaces 936, 938 (FIG. 21).

Turning first to left member 920, as best seen in FIG. 18, member 920 has its outer surface 924 relieved so as to form a pair of needle-receiving, generally arcuate recesses 940A, 940B.

Figure 19:
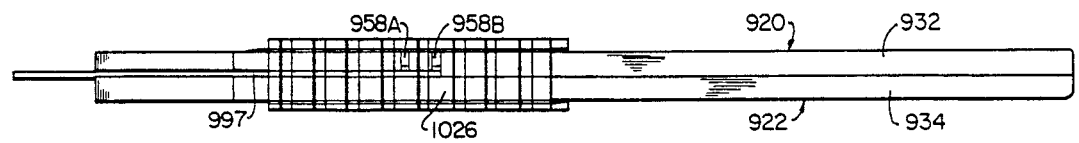
FIG. 19 is a bottom view showing the bottom side of the suture anchor installation tool shown in FIG. 18.

Arcuate recess 940A comprises three coplanar surfaces 942A, 944A and 946A, with surfaces 942A and 944A being separated by a through-hole 948A, and surfaces 944A and 946A being separated by a pair of through-holes 950A and 952A and by a circular well 954A. Well 954A has a floor 956A which is disposed below coplanar surfaces 942A, 944A and 946A. A through-hole 958A adjoins surface 946A and opens on the handle's bottom surface 932, as seen in FIG. 19. Preferably, small ribs 960A extend slightly into arcuate recess 940A, above through-holes 948A and 952A.

Similarly, arcuate recess 940B comprises three coplanar surfaces 942B, 944B and 946B, with surfaces 942B and 944B being separated by a through-hole 948B, and surfaces 944B and 946B being separated by a pair of through-holes 950B and 952B and by a circular well 954B. Well 954B has a floor 956B which is disposed below coplanar surfaces 942B, 944B and 946B. A through-hole 958B adjoins surface 946B and opens on bottom surface 932, as seen in FIG. 19. Preferably, small ribs 960B extend slightly into arcuate recess 940B, above through-holes 948B and 952B.

Member 920 also includes a large through-hole 962 near its rear end (FIG. 18), and an inclined surface stop 964 (FIGS. 18 and 25) forward of its arcuate recesses 940A, 940B.

Figure 22:
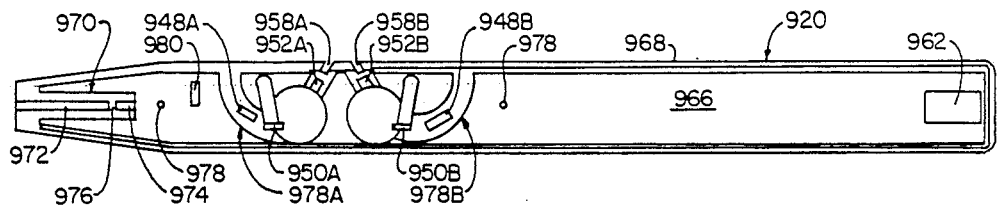
FIG. 22 is a side view in elevation showing the interior configuration of the left half of the suture anchor installation tool shown in FIG. 18.

Looking next at FIG. 22, the interior surface of member 920 comprises a floor 966 from which rises a perimeter wall 968. Perimeter wall 968 has a front extension 970 which is relieved at 972 and 974 so as to form a land 976 therebetween. Also rising out of floor 962 are a pair of generally arcuate-shaped rises 978A, 978B which correspond to arcuate recesses 940A, 940B previously described, and which are penetrated by the through-holes 948A, 948B, 950A, 950B, 952A, 952B, 958A and 958B previously described. Also rising out of floor 924 are a pair of rods 978 and a strut 980.

Member 922 comprises a large through-hole 982 near its rear end (FIGS. 20 and 23), and an elongated slot 984 which extends completely through the member. Member 922 also comprises a surface recess 986 (FIG. 20) formed in its outer surface 926 and surrounding a through-hole 988, and a surface recess 990 formed rearward of recess 986.

Figure 23A:
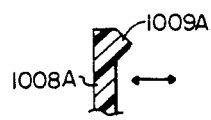
FIG. 23A is a partial sectional view taken along line 23A—23A of FIG. 23.
Figure 23B:
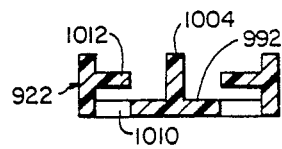
FIG. 23B is a partial sectional view taken along line 23B—23B of FIG. 23.
Figure 23:
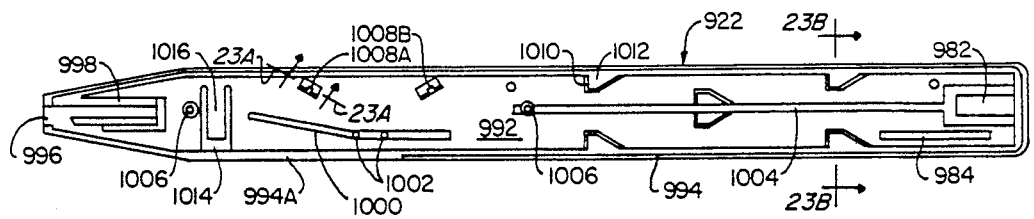
FIG. 23 is a side view in elevation showing the interior configuration of the right half of the suture anchor installation tool shown in FIG. 18.

Looking next to FIG. 23, the interior surface of member 922 comprises a floor 992 from which rises a perimeter wall 994. Perimeter wall 994 extends completely around the perimeter of member 922, except for a small portion at the front of member 922, where an opening 996 is formed in the handle's front wall 938. It is also to be appreciated that perimeter wall 994 is reduced in height at 994A (FIG. 23) relative to the remainder of perimeter wall 994 whereby an elongated slot 997 (FIG. 19) will be created when the two handle members are joined together.

Also rising from floor 992 is a cannula wall 998 which, when the handle's two members 920 and 922 are joined together in the manner hereinafter described, combine with recesses 972 and 974 of member 920 so as to receive cannula 904.

Also rising from floor 992 of member 922 is a suture guide wall 1000 which includes a pair of posts 1002 extending therefrom. It is to be appreciated that posts 1002 are positioned so that they reside adjacent the generally arcuately-shaped rises 978A, 978B of handle member 920 when handle members 920 and 922 are joined together in the manner hereinafter described.

A center wall 1004 also rises from floor 992 of member 922, becoming bifurcated about its rear end so as to surround the large through-hole 982 formed in the rear of member 922. It is to be appreciated that the position of through-hole 982 in member 922 is coordinated with the position of through-hole 962 in member 920 so that the two holes 962 and 982 align with one another when halves 920 and 922 are joined, thereby forming a single hole extending completely through the complete handle member 906.

A pair of hollow posts 1006 (one of which is formed integral with center wall 1004) are also formed about the interior of member 922, with hollow posts 1006 being positioned such that they can receive posts 978 when the two halves 920 and 922 are joined together.

Also rising out of floor 992 of member 922 are a pair of needle-retaining fingers 1008A, 1008B. Needle-retaining fingers 1008A, 1008B are sized and positioned such that they will extend through the through-holes 950A, 950B, respectively, when halves 920 and 922 are joined together, so that the upper portions of fingers 1008A, 1008B can engage and help retain needles contained in the needle-receiving, generally arcuate recesses 940A, 940B. Preferably, fingers 1008A, 1008B include a slight overhang 1009A, 1009B (FIG. 23A) about their top ends which fit up over the top ends of needles received in recesses 940A, 940B. Fingers 1008A, 1008B are formed such that they are easily flexible, whereby they can release any needles contained in recesses 940A, 940B when the needles are pulled upward out of the recesses with a sufficient force.

Figure 20:
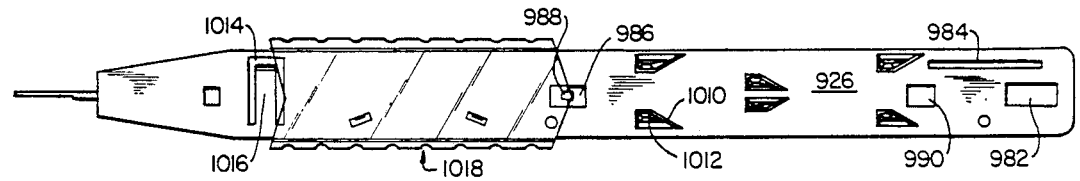
FIG. 20 is a side view in elevation showing the right side of the suture anchor installation tool shown in FIG. 18.

Looking next at FIGS. 20, 23 and 23B, member 922 also includes a plurality of openings 1010 which extend completely through member 922 and a plurality of suture-retaining flanges 1012 which extend from peripheral wall 994 or center wall 1004 and substantially overlie openings 1010. Flanges 1012 are spaced slightly above the floor 992 of member 922 such that suture can be slipped beneath flanges 1012 and will remain there until subjected to a pulling action, whereupon the sutures can be pulled free of the flanges.

Still looking now at FIGS. 20 and 23, member 922 also includes a U-shaped opening 1014 which defines a flexible finger-like flange 1016.

Looking next at FIGS. 18–21, suture anchor installation tool 902 also includes a needle cover 1018 which includes a left wall 1020, a right wall 1022, a top wall 1024 and a bottom wall 1026. Needle cover 1018 is sized so that it will make a close sliding fit over the outside surfaces of the complete handle 906. An inclined stop member 1028 is positioned on the inside rear portion of right wall 1022. Stop member 1028 is adapted to engage recesses 986 and 990 of the handle's right member 922 when needle cover 1018 is slidably fitted over the combined handle member 906, as will hereinafter be described in further detail.

Prior to using the foregoing apparatus in a surgical procedure, the apparatus is assembled as follows.

First, a suture anchor 105, a suture 205, a pair of suture needles 225A, 225B, a cannula 904 and handle members 920 and 922 are fabricated.

Then the suture 205, having free ends 215A, 215B, is attached to the suture anchor 105 by threading the suture around pin 137 so that the intermediate portion 210 of the suture is supported by anchor pin 137 while the two ends 215A, 215B of the suture are left free of the suture anchor.

Then the suture anchor is attached to the installation tool's cannula 904 by fitting the suture anchor's upper portion 112 into the front end of the cannula, with the suture anchor's barb 115 being accommodated in the cannula's slot 914.

Next, the rear end of the cannula is positioned into the appropriate relieved portions in member 920, i.e., the rear end 910 of the cannula is fit into relieved portions 972, 974, with the cannula's rear opening 918 (FIG. 18) receiving handle land 976, whereby the cannula's slot 914 will be oriented upward, toward top surfaces 928 of handle member 920.

Next, an intermediate portion 210 of the suture is passed into the interior of member 922 via front opening 996 so that it passes over flange 1016, to the outside of suture guide wall 1000, under a pair of flanges 1012 and across elongated slot 984 before doubling back adjacent center wall 1004 and under another flange 1012, around the front of center wall 1004, and under another flange 1012. At the rear of member 922 the suture is doubled back again toward the front of the member, back under another pair of flanges 1012. Due to the spacing between flanges 1012 and handle floor 992, suture 205 will be releasably held to handle member 922.

Figure 24:
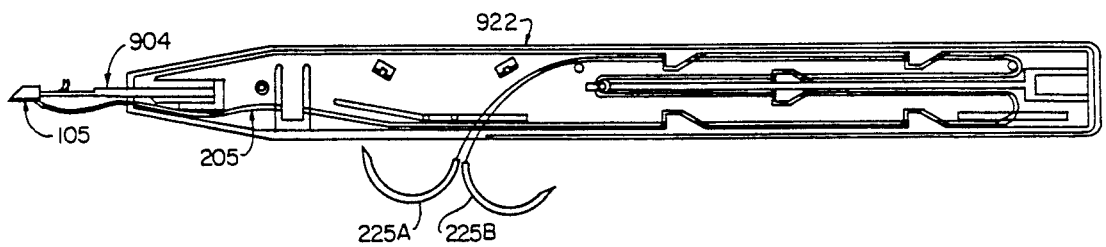
FIG. 24 is a side view in elevation showing the interior configuration of the right half of the suture anchor installation tool, with a suture anchor installed on the front end of the installation tool and a suture loaded into the interior of the installation tool.
Figure 25:
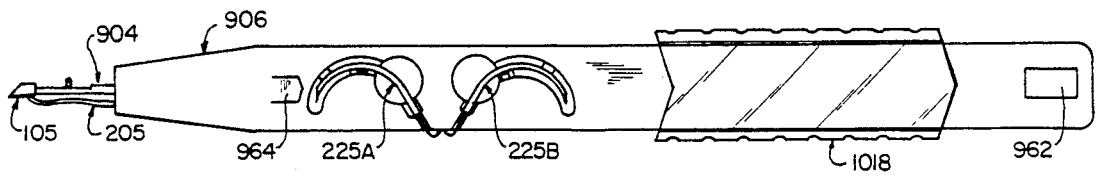
FIG. 25 is a view like that of FIG. 18, except that a suture anchor has been installed on the front end of the installation tool, its accompanying suture has been loaded into the interior of the installation tool, and a pair of surgical needles have been mounted in the outer left side of the installation tool, and the installation tool's needle cover has been moved to its rearward position to expose the surgical needles.
Figure 26:
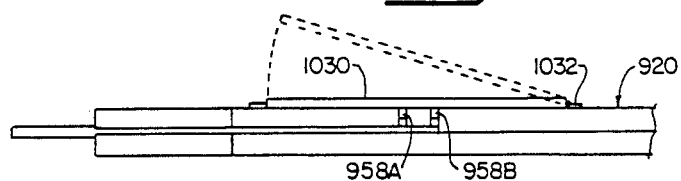
FIG. 26 shows an alternative form of needle cover.

Then a pair of surgical needles 225A, 225B are attached to the free ends 215A, 215B of the suture, if they have not already been attached (FIG. 24).

Next the two handle halves 920 and 922 are joined together, either by mechanically snapping the two members together or by gluing or welding the two members together, so that their peripheral walls come together to form a single handle with a hollow interior, access being had to the interior via front opening 996 and bottom through-holes 958A, 958B. More specifically, when the two halves 920 and 922 come together, rods 978 seat in hollow posts 1006, posts 1002 are positioned so that they reside adjacent the generally arcuately-shaped rises 978A, 978B, needle-retaining fingers 1008A, 1008B extend through the through-holes 950A, 950B, respectively, so that the upper portions of fingers 1008A, 1008B extend into the needle-receiving, generally arcuate recesses 940A, 940B, and strut 980 engages flange 1016. It is to be appreciated that when the two halves 920 and 922 are brought together in the foregoing manner so as to form the complete handle member 906, strut 980 will engage and releasably hold the suture to flexible flange 1016. It is also to be appreciated that when the two halves 920 and 922 are brought together in the foregoing manner so as to form the complete handle member 906, rear openings 962 and 982 are aligned with one another so as to form a single opening extending completely through the handle member. As noted previously, due to the reduced perimeter wall height at 994A (FIG. 23), a slot 997 (FIG. 19) is created (when the two handle members are joined together) which permits access to the interior of the complete handle member. Slot 997 is sized so as to be capable of passing a suture therethrough, and extends between front opening 996 and bottom openings 958A and 958B (FIG. 19).

It is also to be appreciated that when the two halves 920 and 922 are brought together in the foregoing manner so as to form the complete handle member, the intermediate portion of the suture will pass into the interior of handle member 906 via front opening 996 and will pass out of the interior of handle member 906 via the two bottom openings 958A, 958B. Front opening 996, elongated slot 997, and bottom openings 958A, 958B are sized so that the suture is free to slip easily through the openings.

Next the two surgical needles 225A, 225B are fit into needle recesses 940A, 940B so that they rest on coplanar surfaces 942A, 944A, 946A, and 942B, 944B, 946B, respectively. As needles 225A, 225B are fit into recesses 940A, 940B, they deflect and slip past flexible fingers 1008A, 1008B and are captured by the upper ends 1009A, 1009B thereof. When the needles 225A, 225B are positioned in the foregoing manner, they sit below ribs 960A, 960B; these ribs also help keep needles 225A, 225B seated in recesses 940A, 940B until needed.

Then a crochet-like tool (not shown) is inserted into rear slot 984 and is used to pull the intermediate portion of the suture taut within the handle member.

Finally, needle cover 1018 is slipped over the rear end of the assembled handle. Needle cover 1018 is forced forward along the handle until the needle cover's left wall 1020 engages the handle's surface stop 964, whereupon forward movement of the needle cover is impeded. At this point the needle cover completely covers the needles 225A, 225B which are contained within needle recesses 940A, 940B. It is to be appreciated that when needle cover 1018 is in engagement with handle stop 964, the needle cover's inclined stop member 1028 will rest in the handle member's surface recess 986, centered in through-hole 988, whereby needle cover 1018 will be releasably captured in the foregoing position.

Preferably, handle member 922 and needle cover 1018 are formed out of transparent plastic materials so that the suture contained inside the housing and the needles captured in recesses 940A, 940B can be clearly observed during assembly and subsequent use.

The foregoing components may then be packaged, sterilized and stored until required during surgery.

During surgery, the apparatus is used as follows. First, a hole is formed in the bone which is to receive the suture. Then the bone anchor is deployed inside the bone by pressing the distal end of the suture anchor installation tool down into the hole in the bone. Next, the installation tool is withdrawn, leaving the bone anchor in place within the bone. As the installation tool is withdrawn, the intermediate portion of the suture contained within the interior of the installation tool's handle plays out of the handle, via the handle's front opening 996 and/or the handle's elongated slot 997. As this occurs, flange 1016 and flanges 1012 allow the suture to slip beneath them.

Thereafter, if the surgeon is not yet ready to use the needles 225A, 225B to suture tissue to the bone holding suture anchor 105, the installation tool may be laid down near the surgical site. Alternatively, the installation tool's handle may be attached to a surgical drape or other apparatus present about the surgical site so as to make certain that the handle does not slip away. This may be done by passing a tie through the opening 962,982 present in the rear of handle member 906.

When the surgeon is ready to use the surgical needles 225A, 225B to suture tissue to the bone, needled cover 1018 is forced backwards along handle member 906, causing the cover's stop member 1028 to slip out of the handle's surface recess 986 and out of through-hole 988. Needle cover 1018 slips backwards along handle 906 until the cover's stop member 1028 slips into the handle's rear surface recess 990 (FIG. 20), whereupon further rearward movement of the needle cover is impeded. It is to be appreciated that when the needle cover's stop member 1028 is in engagement with the handle's rear surface recess 990 (FIG. 25), the needles 225A, 225B in needle recesses 940A, 940B will be exposed.

Then the surgeon removes needles 225A, 225B from recesses 940A, 940B with a pair of needle-nosed forceps (not shown). More specifically, the surgeon inserts the needle-nosed forceps into well 954A so as to obtain a firm grip on needle 225A, and then pulls the needle upward. This causes the needle to slip past resilient finger 1008A and ribs 960A and out of recess 940A. Needle 225A is pulled away from handle 906 until all of the suture attached to needle 225A is pulled out of handle 906, thereby freeing needle 225A and its associated suture end from the installation tool. The same technique is used to free needle 225B from the installation tool. Once this has been done, installation tool 902 may be discarded.

The needles 225A, 225B and their associated suture lengths may then be used to suture tissue to the bone holding suture anchor 105.

It is, of course, to be appreciated that installation tool 902 might be modified somewhat from that described above and illustrated in FIGS. 18-25, i.e., the installation tool might have its cannula 904 modified somewhat to use a construction such as that shown in FIGS. 15-17.

In this respect, it is noted that the cannulae shown in FIGS. 15 and 16, or the cannula-like rod shown in FIG. 17 might be used with a suture anchor such as the suture anchor 505 shown in FIGS. 13 and 14, i.e., a suture anchor having a constant diameter coupling member, or they might be used with a suture anchor such as that shown in FIGS. 1 and 2, i.e., a suture anchor having a coupling member with a stepped outer configuration.

In the event that a cannula such as that shown in FIG. 15 is used in conjunction with a suture anchor such as that shown in FIGS. 1 and 2, the depth of cannula shoulder 650 could be coordinated with the height of the suture anchor's upper end 112 so that the suture anchor's shoulder 113 engages cannula end surface 630 when the suture anchor's end surface 125 engages cannula shoulder 650, or the depth of cannula shoulder 650 could be coordinated with the height of the suture anchor's upper end 112 so that the suture anchors's shoulder 113 is spaced from cannula end surface 630 when the suture anchor's end surface 125 engages cannula shoulder 650.

Similarly, in the event that a cannula such as that shown in FIG. 16 is used in conjunction with a suture anchor such as that shown in FIGS. 1 and 2, the position of the cannula crimps 750 could be coordinated with the height of the suture anchor's upper end 112 so that the suture anchor's shoulder 113 engages cannula end surface 730 when the suture anchor's end surface 125 engages cannula crimps 750, or the position of the cannula crimps 750 could be coordinated with the height of the suture anchor's upper end 112 so that the suture anchor's shoulder 113 is spaced from cannula end surface 730 when the suture anchor's end surface 125 engages cannula crimps 750.

In a like manner, in the event that a cannula like rod such as that shown in FIG. 17 is used in conjunction with a suture anchor such as that shown in FIGS. 1 and 2, the depth of the flat surface 850 could be coordinated with the height of the suture anchor's upper end 112 so that the suture anchor's shoulder 113 engages rod end surface 830 when the suture anchor's end surface 125 engages flat surface 850, or the depth of flat surface 850 could be coordinated with the height of the suture anchor's upper end 112 so that the suture anchor's shoulder 113 is spaced from rod end surface 830 when the suture anchor's end surface 125 engages rod flat surface 850.

Furthermore, the installation tool 902 might be modified to use a different form of needle cover. By way of example, member 920 might be modified to include a snap cover 1030 joined to member 920 by a flexible hinge 1032. Snap cover 1030 covers needle recesses 940A, 940B and pivots on its hinge 1032 to alternatively cover up or expose needles 225A, 225B contained in needle recesses 940A, 940B.

These and other changes of their type are believed to be obvious to those skilled in the art and within the scope of the present invention.

Advantages Of The Invention

Numerous advantages are achieved by using the present invention.

For one thing, a new and improved suture anchor installation tool is disclosed for deploying suture anchors of the sort described and illustrated in U.S. Patent Applications Ser. Nos. 051,367, 132,940, 308,318 and 449,118.

For another thing, a new and improved suture anchor installation tool is disclosed which is an improvement over the suture anchor installation tools described and illustrated in U.S. Patent Application Ser. No. 449,118.

In addition, a new and improved suture anchor installation tool is disclosed which is adapted to receive a pair of surgical needles in a pair of grooves formed in the outer surface of the installation tool, and which provides means for selectively covering and uncovering the pair of surgical needles received in the pair of grooves.

Also, a new and improved suture anchor installation tool is disclosed which includes improved means for releasably holding a pair of surgical needles in a pair of grooves formed in the outer surface of the installation tool.

In addition, a new and improved suture anchor system is provided for anchoring a piece of conventional suture in bone.

Also, a new and improved method is disclosed for anchoring a piece of conventional suture in bone.

Still other advantages of the invention will be obvious to those skilled in the art.

What is claimed is:

1. A suture anchor installation tool for deploying a suture anchor of the sort comprising (a) a coupling member, (b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and (c) attachment means for attaching a portion of a piece of conventional suture to said suture anchor, said suture anchor installation tool comprising a first body portion and a second body portion, said first body portion having a first end and a second end, said first end of said first body portion being hollow and having a slot extending from said first end of said first body portion towards said second end of said first body portion, said first end of said first body portion being sized to accommodate a portion of said coupling member, and said slot being sized to accommodate said barb of said suture anchor, and said second body portion having a first end and a second end, said second body portion having a hollow interior and an opening leading to said hollow interior, said hollow interior being sized to accommodate an intermediate portion of a suture attached to the suture anchor, and said opening being sized to accommodate at least one cross-section of said suture, with said second end of said first body portion being joined to said first end of said second body portion, said second body portion further including needle receiving means for receiving at least one surgical needle attached to said suture in an outer surface of said second body portion, and said second body portion further including needle covering means for selectively covering and uncovering said needle receiving means.

2. A suture anchor installation tool according to claim 1 wherein said needle covering means is adapted to fit about the exterior of said second body portion and is adapted to move between a first position wherein said needle covering means covers said needle receiving means and a second position wherein said needle covering means does not cover said needle receiving means.

3. A suture anchor installation tool according to claim 2 wherein said needle covering means is adapted to slidably move about the exterior of said second body portion between said first and second positions.

4. A suture anchor installation tool according to claim 3 further comprising first stop means for releasably holding said needle covering means in said first position and second stop means for releasably holding said needle covering means in said second position.

5. A suture anchor installation tool according to claim 2 wherein said needle covering means comprises a snap cover mounted to said second body portion by a hinge.

6. A suture anchor installation tool according to claim 1 wherein said needle receiving means comprises at least one arcuate groove formed in said outer surface of said second body portion, and needle holding means for releasably holding at least one needle in said needle receiving means.

7. A suture anchor installation tool according to claim 6 wherein said needle holding means comprises at least one flexible finger intruding into said at least one arcuate groove and adapted to releasably engage a needle received in said at least one arcuate groove.

8. A suture anchor system for anchoring a piece of conventional suture in bone, said system comprising:
a suture having a pair of ends and an intermediate portion disposed therebetween;
a suture anchor comprising:
(a) a coupling member,
(b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and
(c) attachment means for attaching said suture to said suture anchor so as to leave at least one end of said suture free of said suture anchor;
said suture being attached to said attachment means so as to leave at least one end of said suture free of said suture anchor;
at least one surgical needle attached to said at least one free end of said suture;
a suture anchor installation tool comprising a first body portion and a second body portion,
said first body portion having a first end and a second end, said first end of said first body portion being hollow and having a slot extending from said first end of said first body portion towards said second end of said first body portion, said first end of said first body portion being sized to accommodate a portion of said coupling member, and said slot being sized to accommodate said barb of said suture anchor, and
said second body portion having a first end and a second end, said second body portion having a hollow interior and an opening leading to said hollow interior, said hollow interior being sized to accommodate said intermediate portion of said suture, and said opening being sized to accommodate at least one cross-section of said suture, with said second end of said first body portion being joined to said first end of said second body portion,
said second body portion further including needle receiving means for receiving said at least one surgical needle in an outer surface of said second body portion, and said second body portion further including needle covering means for selectively covering and uncovering said at least one surgical needle received in said needle receiving means, said suture anchor being attached to said first end of said first body portion by fitting a portion of said coupling member into said first end of said first body portion and by fitting said barb of said suture anchor into said slot so that said barb extends away from said first end of said first body portion, through said slot, with said intermediate portion of said suture being stored within said hollow interior and said at least one surgical needle being stored in said needle receiving means and being selectively covered or uncovered by said needle covering means.

9. A system according to claim 8 wherein said needle covering means is adapted to fit about the exterior of said second body portion and is adapted to move between a first position wherein said needle covering means covers said at least one needle stored in said needle receiving means and a second position wherein said needle covering means does not cover said at least one needle stored in said needle receiving means.

10. A system according to claim 9 wherein said needle covering means is adapted to slidably move about the exterior of said second body portion between said first and second positions.

11. A system according to claim 10 further comprising first stop means for releasably holding said needle covering means in said first position and second stop means for releasably holding said needle covering means in said second position.

12. A system according to claim 9 wherein said needle covering means comprises a snap cover mounted to said second body portion by a hinge.

13. A system according to claim 8 wherein said needle receiving means comprises at least one arcuate groove formed in said outer surface of said second body portion, and needle holding means for releasably holding said at least one needle in said needle receiving means.

14. A system according to claim 13 wherein said needle holding means comprises at least one flexible finger intruding into said at least one arcuate groove and adapted to releasably engage said needle received in said at least one arcuate groove.

15. A method for anchoring a piece of conventional suture in bone, said method comprising the steps of:

(1) providing a suture anchor system comprising:

a suture having a pair of ends and an intermediate portion disposed therebetween:

a suture anchor comprising:

(a) a coupling member, (b) at least one barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and (c) attachment means for attaching said suture to said suture anchor so as to leave at least one end of said suture free of said suture anchor;

said suture being attached to said attachment means so as to leave at least one end of said suture free of said suture anchor;

at least one surgical needle attached to said at least one free end of said suture;

a suture anchor installation tool comprising a first body portion and a second body portion, said first body portion having a first end and a second end, said first end of said first body portion being hollow and having a slot extending from said first end of said first body portion towards said second end of said first body portion, said first end of said first body portion being sized to accommodate a portion of said coupling member, and said slot being sized to accommodate said barb of said suture anchor, and said second body portion having a first end and a second end, said second body portion having a hollow interior and an opening leading to said hollow interior, said hollow interior being sized to accommodate said intermediate portion of said suture, and said opening being sized to accommodate at least one cross-section of said suture, with said second end of said first body portion being joined to said first end of said second body portion, said second body portion further including needle receiving means for receiving said at least one surgical needle in an outer surface of said second body portion, and said second body portion further including needle covering means for selectively covering and uncovering said at least one surgical needle received in said needle receiving means, said suture anchor being attached to said first end of said first body portion by fitting a portion of said coupling member into said first end of said first body portion and by fitting said barb of said suture anchor into said slot so that said barb extends away from said first end of said first body portion, through said slot, with said intermediate portion of said suture being stored within said hollow interior and said at least one surgical needle being stored in said needle receiving means and being covered by said needle covering means;

(2) forming a hole in a bone which is to have said suture attached to it;

(3) inserting said first end of said installation tool and said suture anchor into said hole in said bone;

(4) withdrawing said installation tool from said hole in said bone, leaving said suture anchor disposed in said hole and said suture attached to said bone;

(5) manipulating said needle covering means so as to expose said at least one needle received in said needle receiving means; and (6) removing said at least one needle from said needle receiving means.

16. A method according to claim 15 wherein said needle covering means is adapted to fit about the exterior of said second body portion and is adapted to move between a first position wherein said needle covering means covers said at least one needle stored in said needle receiving means and a second position wherein said needle covering means does not cover said at least one needle stored in said needle receiving means.

17. A method according to claim 16 wherein said needle covering means is adapted to slidably move about the exterior of said second body portion between said first and second positions.

18. A method according to claim 17 further comprising first stop means for releasably holding said needle covering means in said first position and second stop means for releasably holding said needle covering means in said second position.

19. A method according to claim 16 wherein said needle covering means comprises a snap cover mounted to said second body portion by a hinge.

20. A method according to claim 15 wherein said needle receiving means comprises at least one arcuate groove formed in said outer surface of said second body portion, and needle holding means for releasably holding said at least one needle in said needle receiving means.

21. A method according to claim 20 wherein said needle holding means comprises at least one flexible finger intruding into said at least one arcuate groove and adapted to releasably engage said needle received in said at least one arcuate groove.

* * * * *

UNITED STATES PATENT AND TRADEMARK OFFICE
CERTIFICATE OF CORRECTION

PATENT NO. : 5,002,550

DATED : March 26, 1991

INVENTOR(S) : Lehmann K. Li

It is certified that error appears in the above-identified patent and that said Letters Patent is hereby corrected as shown below:

Claim 15, col. 21, line 55, the colon should be changed to a semi-colon.

Signed and Sealed this

Fifteenth Day of September, 1992

*Attest:*

DOUGLAS B. COMER

*Attesting Officer*  *Acting Commissioner of Patents and Trademarks*